US009464970B2

(12) United States Patent
Berberich

(10) Patent No.: US 9,464,970 B2
(45) Date of Patent: Oct. 11, 2016

(54) METHOD FOR STAINING A HISTOLOGICAL SAMPLE, AND AUTOMATED STAINER

(71) Applicant: Leica Biosystems Nussloch GmbH, Nussloch (DE)

(72) Inventor: Markus Berberich, Heidelberg (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 170 days.

(21) Appl. No.: 14/022,628

(22) Filed: Sep. 10, 2013

(65) Prior Publication Data

US 2014/0073003 A1    Mar. 13, 2014

(30) Foreign Application Priority Data

Sep. 13, 2012 (DE) .................. 10 2012 216 336

(51) Int. Cl.
*A61B 10/00* (2006.01)
*G01N 1/30* (2006.01)
*G01N 35/00* (2006.01)

(52) U.S. Cl.
CPC .......... *G01N 1/30* (2013.01); *G01N 35/00663* (2013.01); *G01N 2035/00673* (2013.01)

(58) Field of Classification Search
CPC .................. A61B 10/00; G01N 1/30
See application file for complete search history.

(56) References Cited

U.S. PATENT DOCUMENTS

| 4,812,412 | A | 3/1989 | Turner |
| 6,022,746 | A | 2/2000 | Fritchie et al. |
| 2002/0131896 | A1* | 9/2002 | Hunnell ............... G01N 1/31 422/67 |
| 2003/0231791 | A1* | 12/2003 | Torre-Bueno ...... G01N 21/6428 382/133 |
| 2008/0113440 | A1 | 5/2008 | Gurney et al. |
| 2010/0195903 | A1* | 8/2010 | Tani .............................. 382/162 |
| 2012/0009620 | A1 | 1/2012 | Berberich et al. |

FOREIGN PATENT DOCUMENTS

| DE | 10 2008 056 583 B4 | 5/2010 |
| DE | 10 2008 056 584 B4 | 5/2010 |
| WO | 01/46671 A1 | 6/2001 |
| WO | 2008109422 A1 | 9/2008 |
| WO | 2012148893 A1 | 11/2012 |

* cited by examiner

*Primary Examiner* — Jyoti Nagpaul
(74) *Attorney, Agent, or Firm* — Hodgson Russ LLP

(57) ABSTRACT

The invention relates inter alia to an automated stainer for staining, in particular for hemalum-eosin (HE) staining, of a histological sample, the automated stainer exposing the sample to the action of at least one stain using at least one staining parameter. The automated stainer is notable for the fact that the automated stainer comprises an input means with which a staining parameter is definable, in particular is inputtable or is selectable from a plurality of possible staining parameters; and that a control apparatus is present which, upon application of the defined staining parameter, ascertains the prospectively expectable outcome of an action and displays it to the user with a display apparatus, before the automated stainer actually stains the sample.

8 Claims, 1 Drawing Sheet

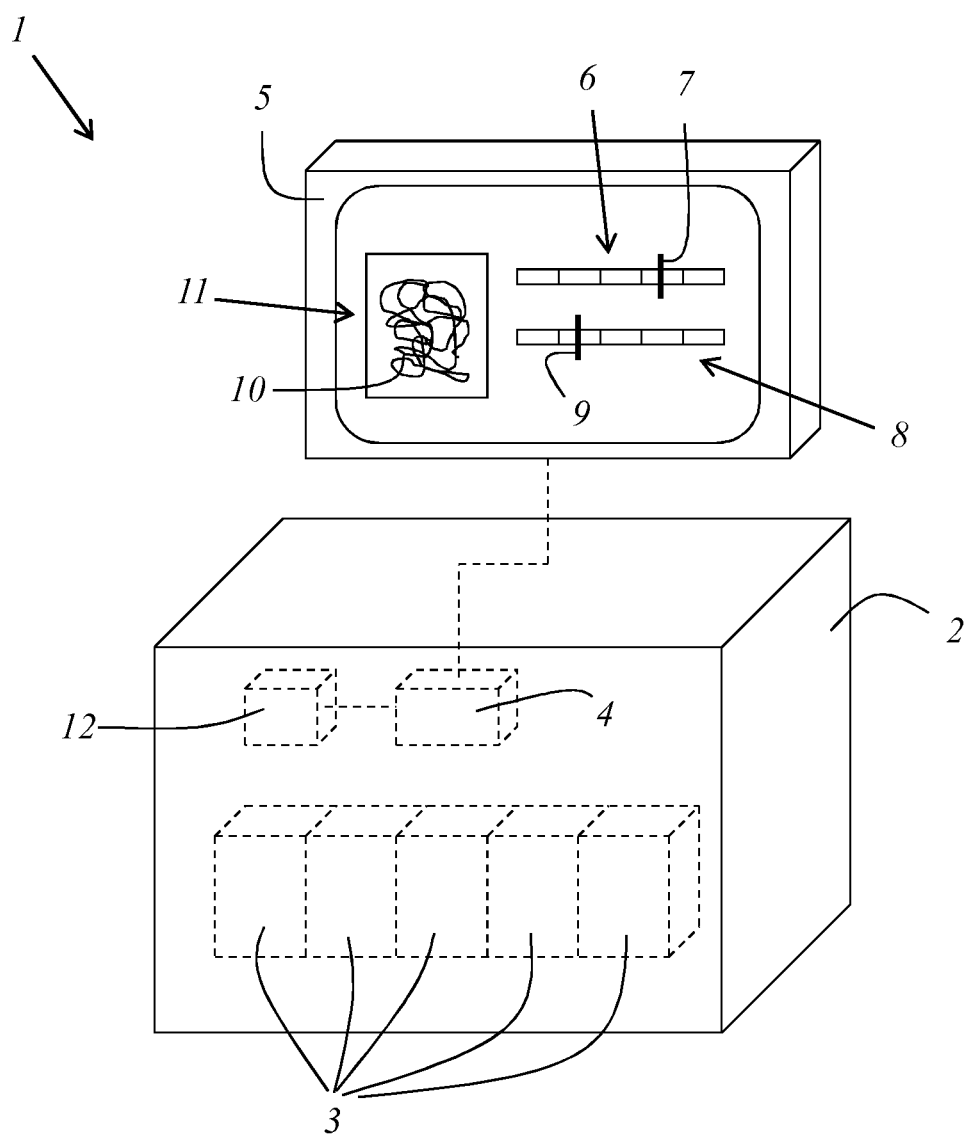

METHOD FOR STAINING A HISTOLOGICAL SAMPLE, AND AUTOMATED STAINER

CROSS REFERENCE TO RELATED APPLICATIONS

This application claims priority of German patent application number 10 2012 216 336.0 filed Sep. 13, 2012, the entire disclosure of which is incorporated by reference herein.

FIELD OF THE INVENTION

The invention relates in particular to a method for staining a histological sample, the sample being exposed to the action of at least one stain using at least one staining parameter. The invention further refers in particular to an automated stainer for staining, in particular for hemalum-eosin (HE) staining, of a histological sample, in which context the automated stainer exposes the sample to the action of at least one stain using at least one staining parameter.

BACKGROUND OF THE INVENTION

In the processing of histological samples, in particular for staining histological samples in the form of tissue sections, the relevant staining parameters are specified and applied by the user, in particular by the operator of a processing apparatus such as, for example, an automated stainer, manually on the basis of his or her experience. The user does not see the outcome of applying the specified parameters until after processing, and an undesired outcome usually can no longer be retrospectively corrected.

Automated apparatuses, for example tissue processors or automated stainers, are often used to process histological samples.

DE 10 2008 056 584 B4, for example, discloses a method and an apparatus for treating histological prepared specimens that preferably are arranged on specimen slides and in specimen slide magazines. The apparatus comprises at least one sensor for acquiring process data relating to time and/or quantity in relation to the specimens and/or to the treatment stations during execution of the treatment program, as well as a device for evaluating the acquired process data after execution of each treatment program and for optimizing the treatment program and/or the processing stations in terms of time and/or quantity based on the evaluation.

DE 10 2008 056 583 B4 discloses a method and an apparatus for identifying reagent quality in devices having multiple treatment stations for the treatment of specimens, in particular of cytological and histological prepared specimens. Provision is made that a carrier element that is equipped with at least one test material is brought together with the specimens in the treatment stations in a predefined sequence. After the last treatment station an evaluation of the test material is made by an evaluation device, such that a reference carrier element having a test material has previously been treated in the reagents of the treatment stations in the predefined sequence; and such that the characteristic properties of the test material caused by the treatment are acquired after the last treatment station and stored as reference data; and such that for evaluation of a test material, the characteristic properties of the test material caused by the treatment are compared with the reference data.

US 2008/0113440 discloses a laboratory system for automatic tissue processing. The laboratory system comprises a conveying unit for selectively transporting, to different processing modules, containers that contain the samples to be processed.

SUMMARY OF THE INVENTION

It is an object of the present invention to provide a method for staining a histological sample that makes possible a good staining outcome even if the user has no knowledge based on experience.

This object is achieved by a method for staining a histological sample, for example, for later microscopic investigation, which is characterized in that a staining parameter is defined; and that the prospectively expectable outcome of an action of the stain is ascertained and displayed upon application of the defined staining parameter, before the sample is actually stained.

A further object of the present invention is to describe an automated stainer for staining a histological sample, which makes possible a good staining outcome even if the user has no knowledge based on experience.

This further object is achieved by an automated stainer which is characterized in that the automated stainer comprises an input means with which a staining parameter is definable and, in particular, can be inputted or is selectable from a plurality of possible staining parameters; and that a control apparatus is present which, upon application of the defined staining parameter, ascertains the prospectively expectable outcome of an action and displays it to the user with a display apparatus, before the automated stainer actually stains the sample.

The invention has the advantage that the user can assess in forward-looking fashion whether the staining parameter or parameters selected by him or her are suitable for achieving the desired processing outcome. A very particular advantage of the invention is that the user can discover, without the worry of performing on the sample an action that is incorrect and possibly cannot be reversed, which staining parameters or which several staining parameters is/are the correct one(s) for his or her specific application and specific sample.

In a particular embodiment of the method, provision is made that a new respective staining parameter is defined or the staining parameter is adjusted and a prospective outcome to be expected upon application of the new staining parameter is ascertained and displayed. This is performed a sufficient number of times until the prospective outcome is coincident with a target outcome.

Provision can be made in particular that an assessment is made by a processing apparatus, in particular including automatically, as to whether the prospective outcome is coincident with a target outcome that is in particular specifiable by the user or selectable from a selection, and initiating an actual staining operation by applying the stain using the defined staining parameter when the prospective outcome is coincident with a target outcome.

In a very particularly advantageous embodiment, the prospective outcome is ascertained in consideration of at least one property of the sample. The property of the sample can be, in particular, the tissue type and/or the tissue size and/or the tissue density and/or the tissue thickness and/or the fat content and/or the water content. Provision can be made that the user inputs the property of the sample, for example using an input means, or that a selection of possible properties of samples is displayed to the user, for example on a screen or on a touch-sensitive screen, from which the user can make a selection.

In an advantageous embodiment, the prospective outcome is retrieved from a memory in which a plurality of expectable outcomes are stored. Provision can also additionally be made in this context that at least one staining parameter or a combination of staining parameters is stored in association with each expectable outcome, and/or that at least one sample property is stored in association with each expectable outcome.

The aforesaid information items are preferably deposited in the memory upon manufacture of an apparatus for processing. Provision can also be made, however, that the user instead or additionally deposits in the memory his or her own expectable outcomes, in each case with associated staining parameters and/or associated sample properties. The user's own expectable outcomes can be based, for example, on actual outcomes that have been respectively obtained by application of the method according to the present invention. For example, the accuracy of the prediction that is displayed can be continuously improved by ongoing supplementing of the information deposited in the memory.

In a particular embodiment, the prospective outcome is displayed on a screen on the basis of a synoptic image of the sample to be processed. The synoptic image can be generated using an image acquisition apparatus, for example using a microscope equipped with an electronic camera. The synoptic image can also be generated, for example, by optical scanning of the sample, for example using a scanning microscope as an image acquisition apparatus.

It is also possible, for example, to obtain a synoptic image using a conventional light microscope. Especially if the sample is not yet stained, it is useful in this context to generate the synoptic image with dark-field illumination and/or with the phase contrast method so that the structures of the sample can be detected at least in preliminary fashion.

Provision can be made that a control apparatus ascertains the prospectively expectable outcome, in particular precalculates it or reads it out from a memory, on the basis of the defined staining parameter and optionally on the basis of at least one sample property, and displays how the synoptic image would change if the user were actually to apply the defined staining parameter or the defined combination of staining parameters. For example, a phase contrast synoptic image that is per se colorless could be displayed in color on a screen, for example by precalculation, in consideration of at least one defined staining parameter, so that the user sees how the sample would look as a result of actually applying the at least one staining parameter.

Alternatively to the generation of a synoptic image of the sample, provision is made in another embodiment that the prospective outcome is displayed on a screen in the form of an exemplary view of an exemplary sample different from the sample to be investigated. Provision can advantageously be made in this context that a plurality of different exemplary views are deposited in the memory. Provision can be made in particular that the exemplary views of exemplary samples which are stored are ones that are similar to the samples actually to be processed and/or have at least one property in common with the samples actually to be processed.

Provision can be made, for example, that an exemplary view of a liver tissue is used in order to display the prospectively expectable outcome with reference to the processing, for example staining, of liver tissue; and that an exemplary view, deposited in the memory, of a prostate tissue is used, for example, in order to display the prospectively expectable outcome with reference to the processing, for example staining, of prostate tissue.

As already mentioned, provision can advantageously be made that in order to define the staining parameter, a selection is made from several possible staining parameters that are, in particular, displayed to the user. Provision can be made, for example, that several possible staining parameters are represented by areas on a screen, from which areas the user can select one or more by clicking thereupon with a mouse or, in the case of a touch-sensitive screen, by touching with a finger, and can thereby define them (optionally can even make a new definition if the prospectively expectable outcome does not correspond to the target outcome).

Provision can be made in particular that several possible staining parameters are represented on a screen by areas that are located next to one another on a line. Provision can be made, for example, that several possible nucleus staining parameters are represented by areas on a screen that are located next to one another, and that further possible counterstaining parameters are represented by a further line of areas on a screen that are located next to one another.

It is also possible for a staining parameter to be defined by value input, for example via a keypad, or by the displacement of a slider depicted on the screen.

As already mentioned, the processing can encompass a staining of the sample for a microscopic investigation. Provision can be made in particular that the displayed prospective outcome is a stain preview.

The staining parameter can, for example, relate to a stain intensity. Provision can in particular also be made that the staining parameter relates to the age of a stain and/or that the staining parameter relates to the chemical composition of a stain and/or that the staining parameter relates to the duration of action of a stain and/or that the staining parameter relates to a quantitative ratio of several stains. A staining parameter can include one or more of these conditions or properties.

As already described with reference to advantageous embodiments, provision can advantageously be made that the method for processing according to the present invention is executed with the aid of an apparatus embodied therefor. Such an apparatus can be, for example, an automated stainer.

In an advantageous embodiment of the apparatus according to the present invention, the display apparatus and/or the input apparatus each comprise a screen. Provision can be made in particular that the input apparatus comprises a touch-sensitive screen. In a particular embodiment, a touch-sensitive screen that serves both as a display apparatus for displaying the prospectively expectable outcome and as an input apparatus is present.

Provision can be made in the context of the apparatus according to the present invention that the control apparatus retrieves the prospective outcome from a memory in which a plurality of expectable outcomes are stored in the manner described above.

The method according to the present invention and/or the apparatus according to the present invention can advantageously be embodied especially for hemalum-eosin (HE) staining of the sample. The invention is, however, in no way restricted to staining or specifically to this staining method.

Provision can advantageously be made that a special staining kit, in particular an HE staining kit, whose properties are also communicated to the automated stainer, is made available to the user. Provision can be made in particular that the properties of the staining kit are stored in a memory medium readable by the automated stainer. The properties of the staining kit can then be taken into consideration as staining parameters (optionally alongside further staining parameters) when ascertaining the prospectively expectable staining outcome. The memory medium can be, for example, a barcode imprinted onto the packaging or onto a container of the staining kit, which barcode can be read out, for example, using an optical scanner. It is also possible for the properties of the staining kit to be stored in an RFID chip arranged on the staining kit, and transferred wirelessly to the automated stainer.

What can be stored in the memory medium can be, for example, when the staining kit was manufactured and/or its chemical composition.

Provision can be made in particular that the staining is accomplished for a subsequent light microscopy investigation and/or that the prospective outcome that is displayed is a staining preview.

The automated stainer can he embodied in particular for staining samples that are arranged, for example after microtome sectioning, on a specimen slide.

BRIEF DESCRIPTION OF THE DRAWINGS

For a fuller understanding of the nature and objects of the invention, reference should be made to the following detailed description taken in conjunction with the accompanying drawings, in which:

FIG. 1 shows an exemplifying embodiment of an apparatus, embodied as an automated stainer, for processing a sample.

DETAILED DESCRIPTION OF THE INVENTION

FIG. 1 shows an exemplifying embodiment of an apparatus, embodied as an automated stainer 1, for processing a sample. Automated stainer 1 comprises a housing 2 that contains a plurality of containers 3 for the different components of an HE staining kit. In a staining process, the samples (not depicted) provided for staining are automatically introduced, under the control of a control apparatus 4 and with the application of predefined staining parameters, successively into the various containers 3. Two of the staining parameters applied here, namely the nucleus stain intensity and the counterstain intensity, are determined before an actual staining operation is carried out, as follows:

Firstly the user selects, on a screen 5 that is embodied as a touch-sensitive screen, a (provisional) nucleus stain intensity and a (provisional) counterstain intensity. For this purpose, several possible nucleus stain parameters are represented by areas located next to one another in a first line 6 on screen 5. One of these nucleus staining parameters, and thus a nucleus stain intensity, can be (provisionally) defined by displacing a first marking 7 along first line 6. Different counterstaining parameters are represented in a second line 8 by areas located next to one another on screen 5. By displacing a second marking 9 along second line 8, the user can (provisionally) define one of these counterstaining parameters and thus a counterstain intensity.

In addition, the user inputs the properties of the sample, in particular the kind of sample, via a keyboard (not depicted).

Provision can moreover be made that the properties of the staining kit are communicated to automated stainer 1, preferably by automatic readout of a barcode arranged on the delivery packaging of the staining kit or of an RFID chip, and are taken into consideration by control apparatus 4 in the context of the further steps.

Control apparatus 4 ascertains, in consideration of the inputted sample properties and in consideration of the properties of the staining kit, the staining outcome that would prospectively be expected upon application of the (provisionally) defined staining parameters, while the sample is not actually stained. The prospectively expectable staining outcome is then displayed to the user, in the form of a staining preview 10, in a window 11 on screen 5.

In order to ascertain the prospectively expectable staining outcome, control apparatus 4 accesses a memory 12 in which a plurality of expectable outcomes are stored, at least the relevant staining parameters (in particular nucleus staining parameters and counterstaining parameters), as well sample properties and staining kit parameters, being associated with and stored for each expectable outcome. Alternatively, the prospectively expectable staining outcome could be precalculated by the control apparatus in consideration of the defined staining parameters and of the inputted sample properties, and the staining outcome could be precalculated in consideration of the properties of the staining kit.

If the displayed expected staining outcome corresponds to the user's requirements and/or is coincident with a target outcome, the actual staining process constituting the action of the staining kit on the sample can be initiated, in which context control apparatus 4 applies the defined staining parameters in the staining process.

If the displayed expectable staining outcome does not correspond to the user's requirements and/or is not coincident with a target outcome, new staining parameters are defined and a staining outcome prospectively expectable upon application of the new staining parameters is ascertained and displayed. This procedure is repeated until the displayed expected staining outcome corresponds to the user's requirements and/or is coincident with a target outcome. Provision can also be made in particular that the automated stainer itself performs this assessment.

The invention is not to be limited to the specific embodiments disclosed, and modifications and other embodiments are intended to be included within the scope of the invention.

LIST OF REFERENCE NUMERALS

1 Automated stainer
2 Housing
3 Container
4 Control apparatus
5 Screen
6 First line
7 First marking
8 Second line
9 Second marking
10 Staining preview
11 Window
12 Memory

What is claimed is:

1. An automated stainer for staining, in particular for hemalum-eosin (HE) staining, of a histological sample, the automated stainer exposing the sample to the action of at least one stain using at least one staining parameter, wherein the automated stainer comprises:

an input apparatus with which a staining parameter is defined by a user or selected from a plurality of possible staining parameters; and a control apparatus which, upon definition or selection of the staining parameter, is configured to ascertain a prospective expected outcome of an action of the staining parameter and display the prospective expected outcome to the user with a display apparatus before the automated stainer stains the sample.

2. The automated stainer according to claim 1, wherein the display apparatus comprises a touch-sensitive screen.

3. The automated stainer according to claim 1, wherein the input apparatus comprises a touch-sensitive screen.

4. The automated stainer according to claim 1, wherein the control apparatus retrieves the prospective expected outcome from a memory storing at least one of:
   (i) a plurality of expected outcomes;
   (ii) a plurality of expected outcomes, the staining parameter or a combination of the staining parameters being stored in association with each of the plurality of expected outcomes; and
   (iii) a plurality of expected outcomes, at least one sample property being stored in association with each of the plurality of expected outcomes.

5. The automated stainer according to claim 1, further comprising an image acquisition apparatus which generates a synoptic image of the sample by at least one of optical scanning of the sample, dark-field illumination of the sample, and use of a phase contrast method, wherein the control apparatus displays the prospective expected outcome on the basis of the generated synoptic image.

6. The automated stainer according to claim 1, wherein the control apparatus displays the prospective expected outcome in the form of an exemplary view of an exemplary sample different from the sample.

7. The automated stainer according to claim 1, wherein the staining parameter relates to at least one of an age of the stain; a chemical composition of the stain; a duration of action of the stain; and a quantitative ratio of several stains.

8. A staining kit, in particular a hemalum-eosin (HE) staining kit, wherein the staining kit comprises:
   a medium configured to store a plurality of staining parameters;
   an input apparatus with which one of the plurality of staining parameters is selected; and
   a control apparatus which, upon selection of the staining parameter, is configured to ascertain a prospective expected outcome of an action of the staining parameter and display it to a user with a display apparatus before actually staining a sample.

* * * * *